US005458569A

United States Patent [19]
Kirk, III et al.

[11] Patent Number: 5,458,569
[45] Date of Patent: Oct. 17, 1995

[54] WEARABLE IONTOPHORESIS SYSTEM

[75] Inventors: Karl D. Kirk, III, New York, N.Y.; James R. Toleman, Palo Alto, Calif.; Robert P. Pandorf, Tenafly, N.J.; Ellen R. Cohen, New York, N.Y.

[73] Assignee: Becton Dickinson and Company, Franklin Lakes, N.J.

[21] Appl. No.: 73,923

[22] Filed: Jun. 8, 1993

[51] Int. Cl.⁶ ...................................................... A61N 1/30
[52] U.S. Cl. .............................................. 604/20; 607/149
[58] Field of Search ............................... 604/20; 607/149, 607/151

[56] References Cited

U.S. PATENT DOCUMENTS

| | | |
|---|---|---|
| 4,622,031 | 11/1986 | Sibalis ........................................ 604/20 |
| 4,700,997 | 10/1987 | Strand . |
| 4,725,263 | 2/1988 | McNichols et al. ........................ 604/20 |
| 4,856,188 | 8/1989 | Sibalis ........................................ 604/20 |
| 4,865,566 | 9/1989 | Rasmussen . |
| 4,919,648 | 4/1990 | Sibalis ........................................ 604/20 |
| 4,931,046 | 9/1990 | Newman .................................... 604/20 |
| 4,942,883 | 7/1990 | Newman .................................... 604/20 |
| 4,950,229 | 8/1990 | Sage, Jr. .................................... 604/20 |
| 5,135,479 | 8/1992 | Sibalis et al. .............................. 604/20 |
| 5,224,928 | 7/1993 | Sibalis et al. .............................. 604/20 |

FOREIGN PATENT DOCUMENTS

8607269  12/1986  WIPO ...................................... 604/20

Primary Examiner—C. Fred Rosenbaum
Assistant Examiner—Chalin Smith
Attorney, Agent, or Firm—Allen W. Wark

[57] ABSTRACT

A wearable iontophoresis system includes a control housing having a connector and an iontophoretic drug delivery patch for placement against the skin of a patient. The patch has a device for retaining the control housing connector which permits the connector to be removably attached to the patch. The control housing also has at least a power supply device and a current delivery device. The control housing has top and bottom surfaces wherein the top surface has raised, recessed and sloping regions. The thickness of the connector is tapered from a second end to a first end. Furthermore, the second end of the connector is attached to the control housing and oriented so that the first end is unattached to the control housing and proximate to the control housing bottom surface. The iontophoretic drug delivery patch includes top and bottom surfaces wherein mounted to the top surface is the device for retaining the control housing connector. The control housing connector retaining device has first and second open ends and a cavity for placement therein of the connector. The taper of the connector permits it to be easily inserted through one of the first and second open ends and into the control housing connector retaining device cavity.

27 Claims, 5 Drawing Sheets

WEARABLE IONTOPHORESIS SYSTEM

BACKGROUND OF THE INVENTION

1. Field of the Invention

The present invention relates to iontophoretic drug delivery systems for transdermally delivering a drug or medicine to a patient, and more specifically relates to an iontophoretic drug delivery system wherein a control housing, having electrical control components therein, is removably mounted to a drug delivery patch.

2. Description of the Prior Art

Iontophoresis may be defined as the passing of chemicals through skin without mechanical puncturing. The chemicals to be infused are in the form of a solution of ions which are stored proximate to a small electrode placed on the surface of the skin. An electric field is produced by the electrode which acts on the charged chemical particles and causes them to diffuse through the skin.

The use of devices for iontophoretic transdermal delivery of drugs are known in the art. Reference to or disclosure of devices for transdermal delivery of drugs by application of electric current through the skin of a person or animal are shown in a number of U.S. patents including U.S. Pat. No. 4,820,263 which issued to Richard Spevak, et al. However, many of the known iontophoretic systems include a control unit which is distally located from the electrode structure that delivers the medication to a specific body location of an individual. The distally located control unit tends to be cumbersome to the individual being treated due to cables and connectors which are required to interconnect the electrode structure to the control system components. The conventional transdermal drug delivery systems, while somewhat portable in nature, were intended for use in a hospital or physician's office. Therefore, these systems are not readily used by patients outside of a supervised environment during the patient's normal daily activities.

Developments in the iontophoretic drug delivery industry have produced drug delivery systems (control unit and corresponding electrode patch) which are portable in nature. However, the control unit of these drug delivery systems are an integral part of the electrode patch structure. In addition, the control unit tends not to be readily separable from the patch which delivers the medicine. Other drug delivery units have been developed wherein the control portion is not integral with the patch. However, these detachable control portions tend to be difficult to properly couple to the patch and they are not entirely user friendly.

OBJECTS AND SUMMARY OF THE INVENTION

It is an object of the present invention to provide an iontophoresis system which can be readily used during a patient's normal daily activities.

It is another object of the present invention to provide a user friendly iontophoresis system in which a control module can be easily and removably mounted to a drug delivery patch irrespective of the orientation of the drug delivery patch on the user.

It is yet another object of the present invention to provide an iontophoresis system which can be easily worn by a patient.

It is still another object of the present invention to provide an iontophoresis system including a drug delivery patch wherein a region of the drug delivery patch which provides medicine to the skin of a patient is identifiable from an elevated view of the patch.

It is a further object of the present invention to provide an iontophoresis system which overcomes the inherent disadvantages of known iontophoretic systems.

In accordance with one form of the present invention, a wearable iontophoretic drug delivery system includes a control housing having connector means. The drug delivery system also includes an iontophoretic drug delivery patch for placement against the skin of a patient. The patch includes means for retaining the control housing connector such that the connector can be removably mounted to the patch.

The control housing, which is to be mounted to the iontophoretic drug delivery patch, contains at least power supply means, current delivery means, and the connector. The control housing has top and bottom surfaces wherein the top surface has raised, recessed and sloping regions. The raised and recessed areas are substantially parallel and non-coplanar, and are connected by the sloping area which is substantially non-parallel to the raised and recessed areas. The connector means is attached to the housing and oriented such that a second end of the connector is mounted to the control housing and a first end of the connector is unattached and proximate to the bottom surface of the housing. The thickness of the first and second ends of the connector are unequal such that the connector thickness tapers from the second mounted end to the first unattached end.

The iontophoretic drug delivery patch is flexible and includes top and bottom surfaces wherein mounted to the top surface is the control housing connector retaining means. The connector retaining means includes a substantially planar base portion and a non-planar top portion. The non-planar top portion and planar base portion define a connector retaining means cavity having first and second open ends.

The present invention is designed so that the first end of the connector means of the control device can be easily inserted through either the first or second open ends of the connector retaining means and into the connector retaining means cavity. The tapering thickness of the connector permits it to be easily inserted through one of the first and second ends and into the connector retaining means cavity. In addition, the thickness of the connector proximate to the second end insures that, when the first end is inserted in the connector retaining means cavity, the connector will enter the cavity only to a point wherein the control housing and iontophoretic drug delivery patch are electrically coupled.

These and other objects, features and advantages of the present invention will become apparent from the following detailed description of the illustrative embodiments thereof, which is to be read in connection with the accompanying drawings.

DETAILED DESCRIPTION OF THE PREFERRED EMBODIMENTS

Figure 1:
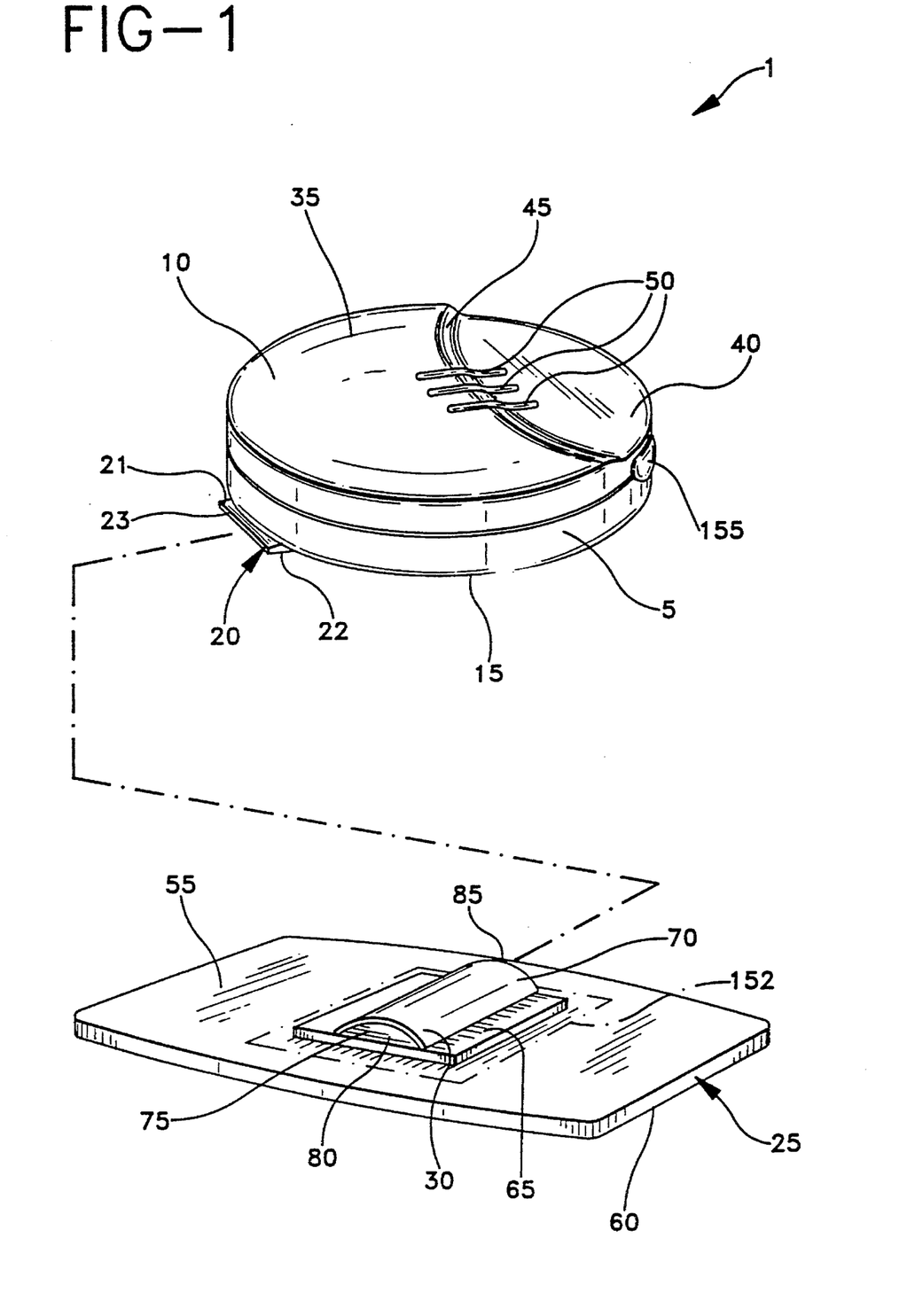
FIG. 1 is an elevated perspective view of the wearable iontophoretic drug delivery system of the present invention wherein the control housing is detached from the iontophoretic drug delivery patch.

Referring initially to FIG. 1 of the drawings, a wearable iontophoretic drug delivery system 1 basically includes a control housing 5 having top and bottom surfaces 10, 15 and connector means 20 having top and bottom surfaces 21, 22 and first and second ends 23, 24 for attachment to an iontophoretic drug delivery patch 25 having means 30 for retaining the control housing connector. The iontophoretic drug delivery system 1 of the present invention is designed so that the control housing 5 can be easily manipulated, including being mounted to and separated from the iontophoretic drug delivery patch 25.

Figure 2A:
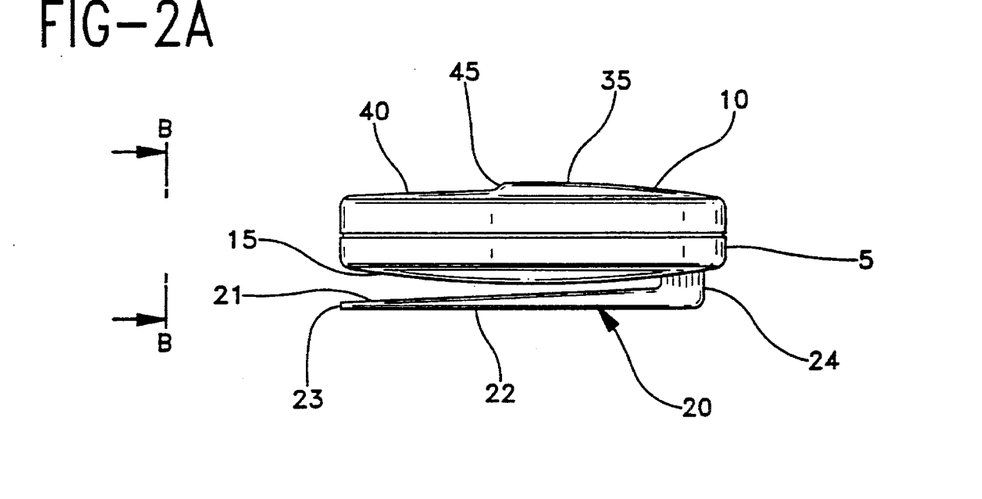
FIG. 2A is a side view of the control housing of the present invention showing the tapered thickness of connector means and a point of attachment of the connector means to the control housing.

One form of the wearable iontophoretic drug delivery system 1 is illustrated in FIG. 1. The control housing 5 of the present invention preferably includes top and bottom surfaces 10, 15 wherein the connector means second end 24 is attached, and the connector means first end 23 is unattached and proximate to the bottom surface 15 of the control housing 5 as shown in FIG. 2A. In addition, FIG. 2A shows a tapering thickness of the connector means from second end 24 to first end 23. In a preferred embodiment, the control housing top surface 10 includes a substantially raised region 35, a substantially recessed region 40 and a substantially sloping region 45. The raised and recessed regions 35, 40 are generally substantially parallel with one another and are configured so that they are non-coplanar. The raised and recessed regions 35, 40 are coupled by the sloping region 45.

Figure 2B:
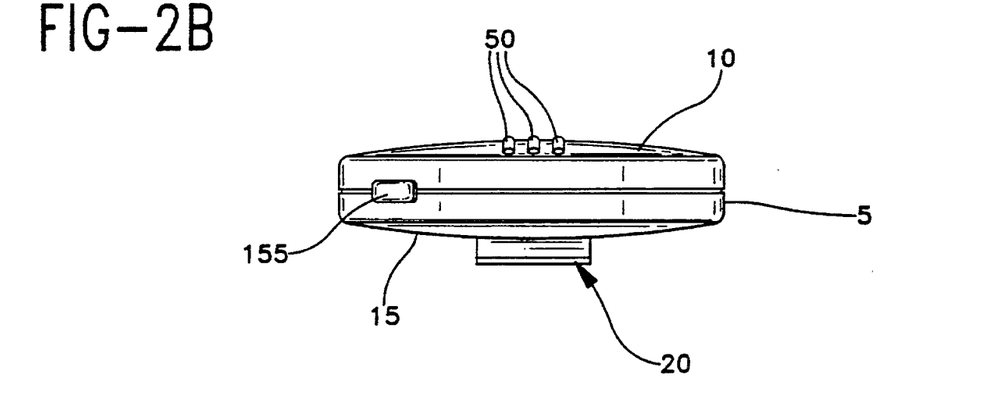
FIG. 2B is a side view of the control housing of the present invention taken along the direction of arrows B—B of FIG. 2A showing the visual accessibility of indicator lights from a direction parallel, and proximate to, a recessed top surface region of the control housing.
Figure 2C:
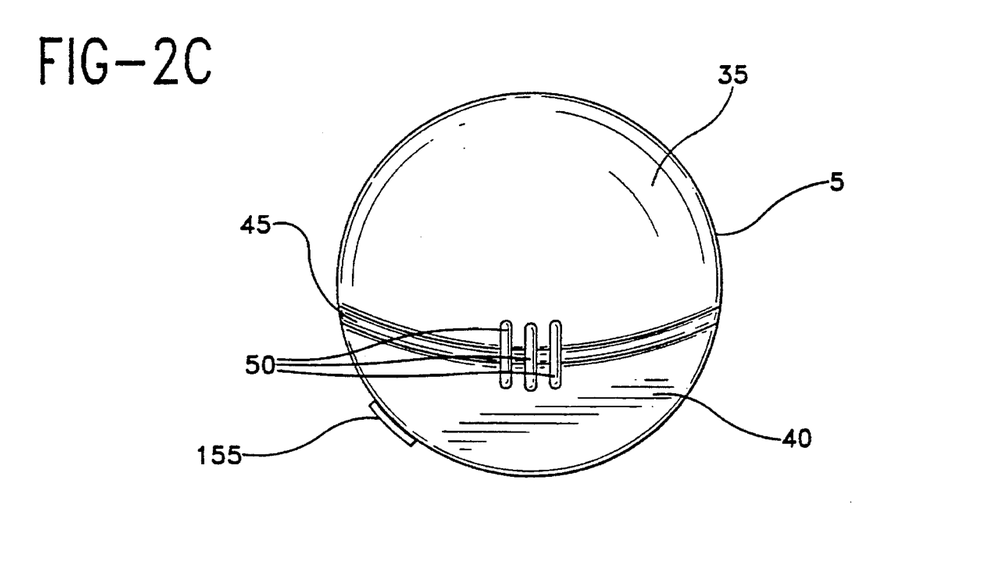
FIG. 2C is a top plan view of the control housing of the present invention showing the visual accessibility of indicator lights from a direction substantially perpendicular to a top surface of the control housing.

In a preferred embodiment of the present invention, indicator lights 50 are located along a portion of the raised region 35, the sloping region 45 and the recessed region 40 of the top surface 10 of the control housing 5. The indicator lights 50 are preferably light emitting diodes (LED's). The indicator lights 50 are configured on the control housing 5 such that they can be viewed along at least one direction which is substantially parallel to the top surface 10 of the control housing 5 and along at least one direction which is substantially perpendicular to the top surface of the control housing 5. FIGS. 2B and 2C respectively show the visual accessibility of the indicator lights 50 from positions which are substantially parallel and perpendicular to the top surface 10 of the control housing 5.

Figure 4:
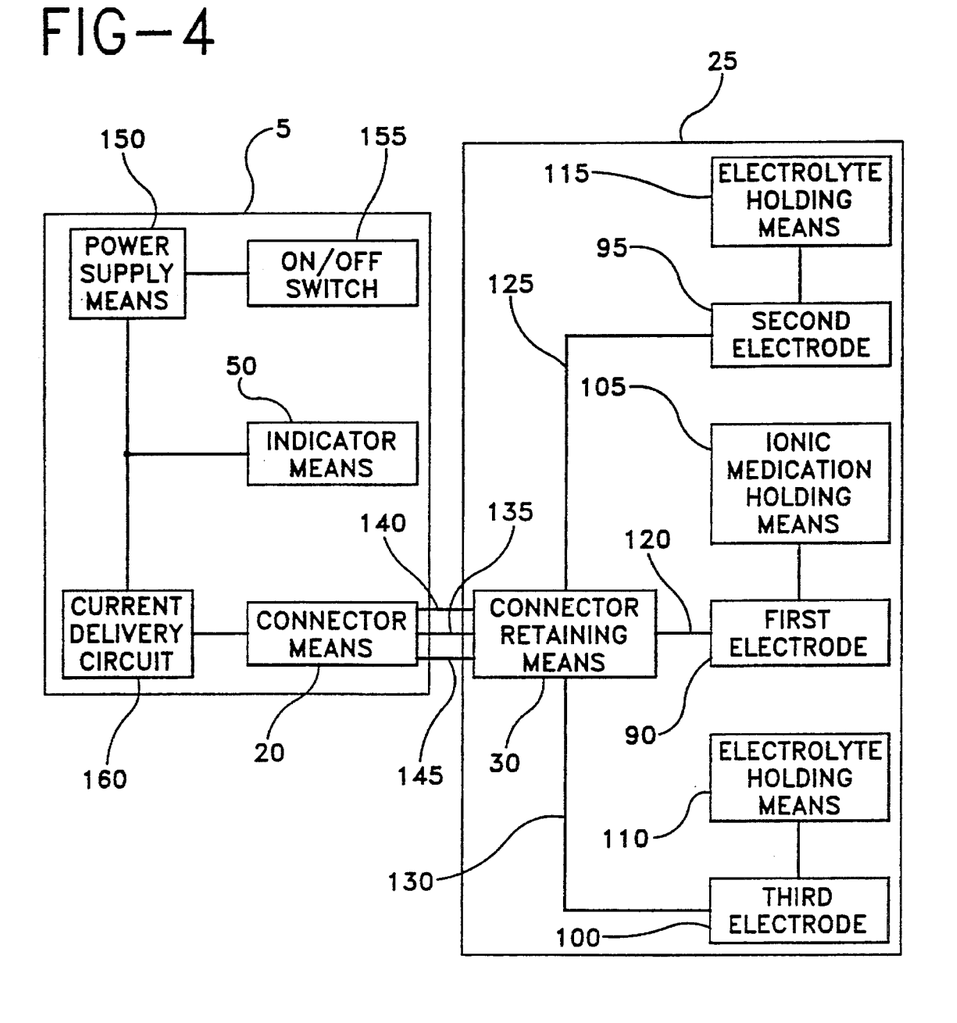
FIG. 4 is a block diagram of one electrical interconnection scheme between the components of the control device and the components of the iontophoretic drug delivery patch.

In a preferred embodiment and as shown in FIG. 4, the indicator means 50 are electrically coupled to both the power supply means 150 and current delivery means 160 so as to monitor whether the iontophoretic drug delivery system is currently operating and whether it is operating properly. Other suitable connections of the indicator means, as known in the art, can be incorporated to monitor additional individual components of the drug delivery system.

As shown in FIG. 1, the iontophoretic drug delivery patch 25, which is designed to be secured to the skin of a patient, basically includes top and bottom surfaces 55, 60. Preferably, the iontophoretic drug delivery patch 25 is constructed with non-rigid materials so that the patch is flexible in order that it conforms to the contour of the portion of the patient's body to which the patch is attached. The top surface 55 of the patch also includes connector retaining means 30. The connector retaining means 30 basically includes a substantially planar base portion 65 and a non-planar top portion 70. In a preferred embodiment, the non-planar top portion has an arch-like shape. The base portion 65 and arch-like top portion 70 can be made as individual parts and thereafter joined together. In the alternative, the base portion 65 and arch-like top portion 70 can be manufactured as a single item. The base portion 65 and arch-like top portion 70 define a connector retaining means cavity 75 having first and second open ends 80, 85 for accepting at least partial placement of the connector means 20 therein.

Figure 3:
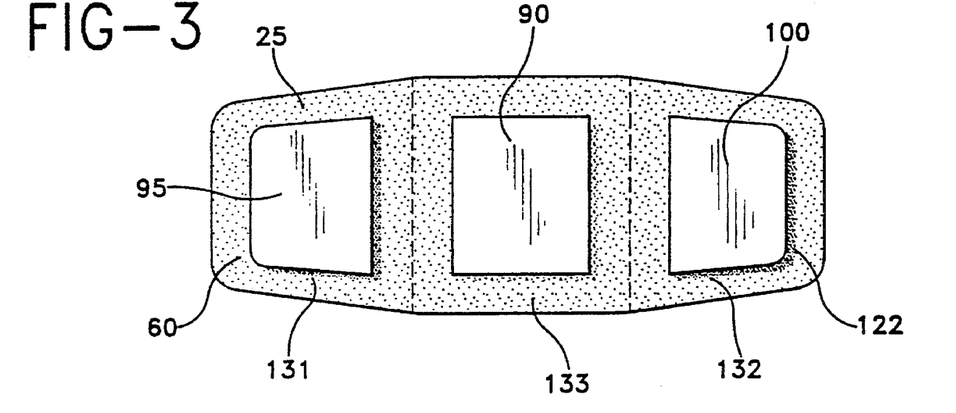
FIG. 3 is a bottom plan view of the iontophoretic drug delivery patch showing an arrangement of electrodes on the bottom surface of the iontophoretic drug delivery patch.

As shown in FIGS. 3 and 4, in a preferred form of the present invention, the iontophoretic drug delivery patch 25 also includes a first electrode 90, which may act as an anode, and second and third electrodes 95, 100, which may be symmetrically placed proximate to the first electrode 90 and both of which may act as cathodes. The patch may also include ionic medication holding means 105 or other container structure for holding an ionic medication situated in relation to the first electrode such that the ionic medication is in electrical communication with the first electrode 90. The drug delivery patch may also include first and second electrolyte holding means 110, 115, or other suitable structure situated in relation to the second and third electrodes such that the electrolyte held by the electrolyte holding means 110, 115 is in electrical communication with the second and third electrodes 95, 100. Preferably, both the ionic medication holding means 105 and the electrolyte holding means 110, 115 are constructed so as to be contained within the structure of the iontophoretic drug delivery patch 25 as known in the art. However, the ionic medication holding means and first and second electrolyte holding means may be situated on the top or bottom surface of the patch so long as the respective holding means is electrically coupled to the appropriate electrode in order to provide the medicine or electrolyte to the skin of the user. In an alternative embodiment, the second electrolyte holding means 115 may be excluded so that only one electrolyte holding means is coupled so as to supply electrolyte to both the second and third electrodes.

As shown in FIG. 1 and previously described, the iontophoretic drug delivery patch 25 has top and bottom sides 55, 60. The first, second and third electrodes 90, 95, 100 are preferably positioned on the bottom side 60 of the patch 25 as shown in FIG. 3 so that the anode 90 and cathodes 95, 100 are in electrical communication with a patient when the bottom side of the patch is appropriately placed against an intended applied area of the patient. As shown in FIG. 3, the second and third electrodes 95, 100, which are the cathodes of the wearable iontophoretic drug delivery system of the present invention, have substantially the same shape and are symmetric about the first electrode 90. This configuration can be characterized as a split cathode arrangement. In addition, adhesive means 122 may be applied to portions of the bottom side of the patch 25 that do not correspond to the first, second and third electrodes so that the patch can be easily secured to the patient. Alternatively, a strap (not shown) or other suitable means can be included in place of or in conjunction with the adhesive 122 in order to secure the patch 25 in place on the user's body.

Figure 5A:
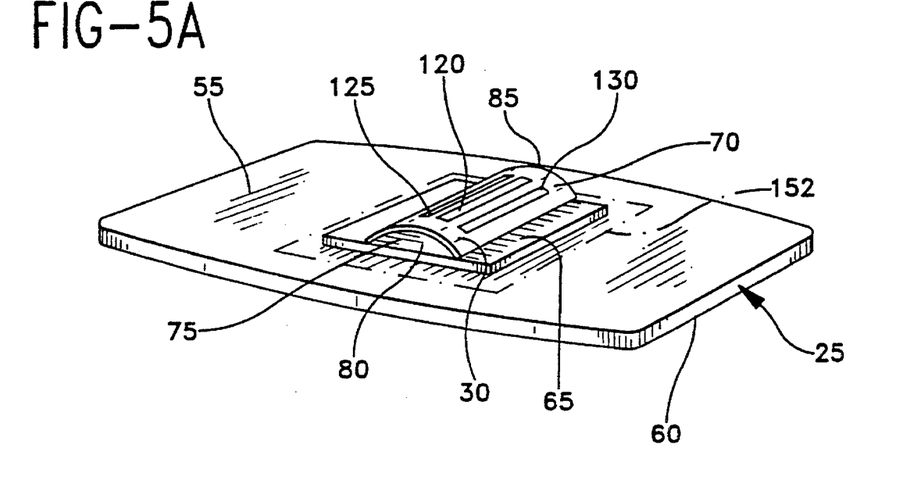
FIG. 5A is an elevated perspective view of the iontophoretic drug delivery patch of the present invention showing one arrangement of the patch electrical contacts.
Figure 5B:
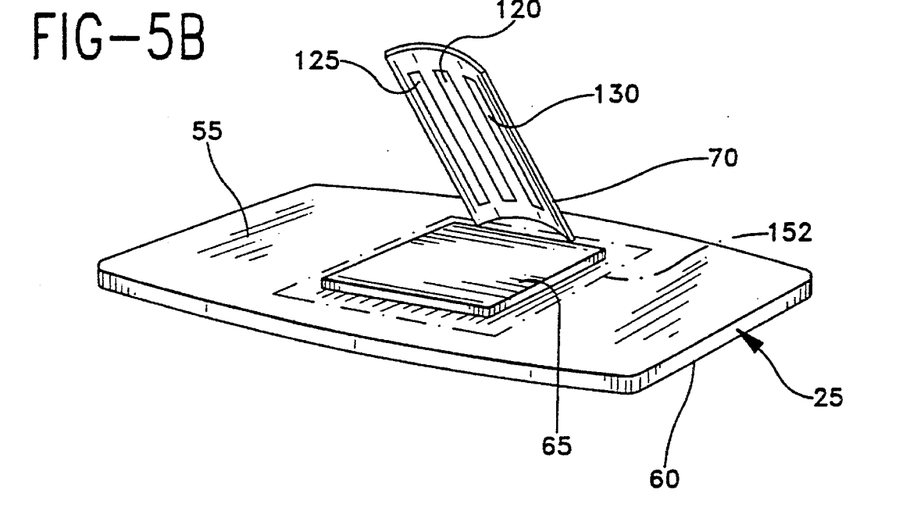
FIG. 5B is an elevated perspective view of the iontophoretic drug delivery patch of the present invention showing a second arrangement of the patch electrical contacts.
Figure 5C:
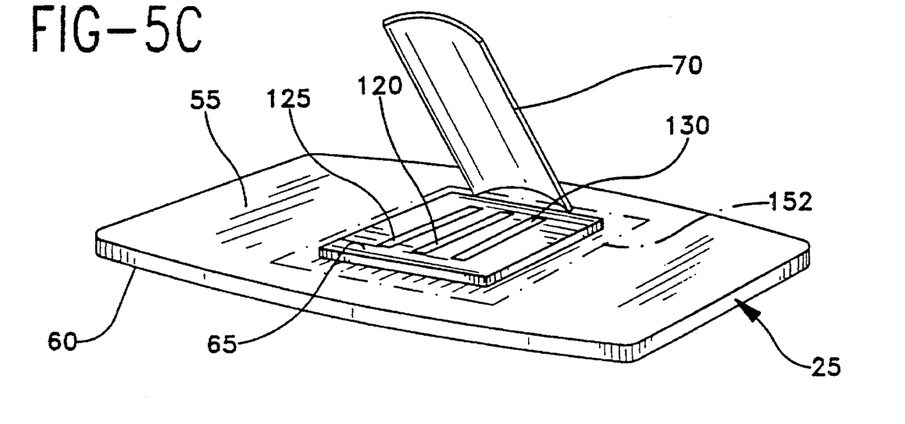
FIG. 5C is an elevated perspective view of the iontophoretic drug delivery patch of the present invention showing a third location of the patch electrical contacts.

As previously stated with regard to FIG. 1, the iontophoretic drug delivery patch 25 includes connector retaining means 30 secured to the top surface 55 of the iontophoretic drug delivery patch 25. As shown in FIGS. 5A, 5B and 5C, the connector retaining means 30 has at least two, and preferably three electrical contacts (three contact arrangement) 120, 125, 130 in electrical communication with the first, second and third electrodes 90, 95, 100 respectively. In the preferred embodiment, the connector retaining means 30 takes the form of a female connector with cavity 75 as shown in FIG. 1 having first and second open ends 80, 85. The electrical contacts of the patch may be located at a variety of locations on the connector retaining means. The electrical contacts 120, 125, 130 may be located on the top exterior surface of the arch-like top portion 70 of the connector retaining means 30 as shown in FIG. 5A. Alternatively, the electrical contacts may be located on an interior cavity surface (either of the arch-like portion 70 as shown in FIG. 5B or the planar base portion 65 as shown in FIG. 5C) or both exterior and interior surfaces of the connector retaining means so that a variety of control housings having differently positioned electrical contacts can be utilized.

It should be noted that the size of the iontophoretic drug delivery patch 25 can vary greatly depending upon the amount of medicine to be delivered and the size of the intended area of the patient to be treated. Therefore, an iontophoretic drug delivery patch for placement against the torso or other large surface of a patient might be larger than a patch for use on the arm or hand of the user. The patch is also designed to have tapered angulated end sections 131, 132 and constant width section 133 as shown in FIG. 3 so that the patch can be more easily attached to areas of the user's body which require a high degree of flexibility. The tapered angulated patch is not as restrictive as non-tapered patches and this design permits movement for the user even when it is secured.

As shown in FIG. 2A, in a preferred embodiment the control housing 5 has connector means 20 attached to the bottom side 15 of control housing. The connector means 20 is coupled to the control housing 5 so that the connector means (and control housing) can be easily mounted to the connector retaining means 30 for electrically coupling the control housing to the iontophoretic drug delivery patch 25. The control housing 5 includes at least two, and preferably three, electrical contacts 135, 140, 145 such that when the connector means 5 is inserted within the cavity 75 of the connector retaining means 30, the first, second and third electrical contacts 120, 125, 130 of the iontophoretic drug delivery patch 25 will be electrically coupled to the first, second and third electrical contacts 135, 140, 145 of the control housing 5.

Figure 6A:
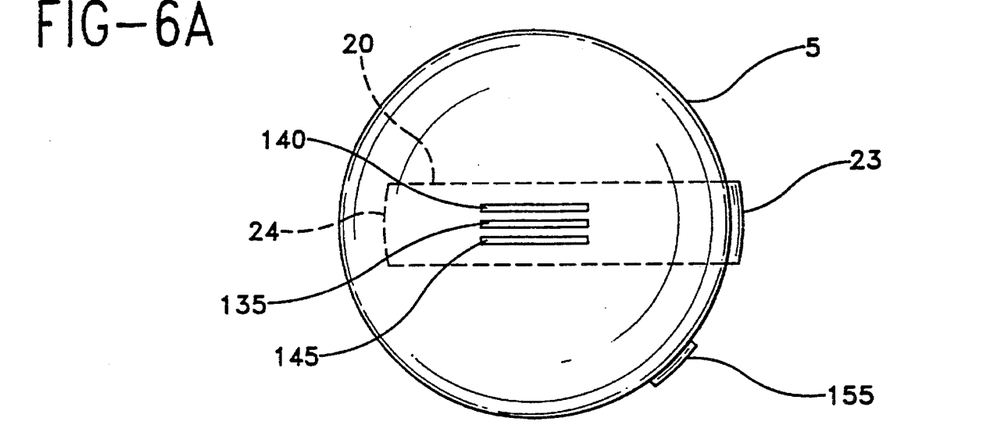
FIG. 6A is a bottom plan view of the wearable iontophoresis system of the present invention with connector means in phantom showing one arrangement of the control housing electrical contacts.
Figure 6B:
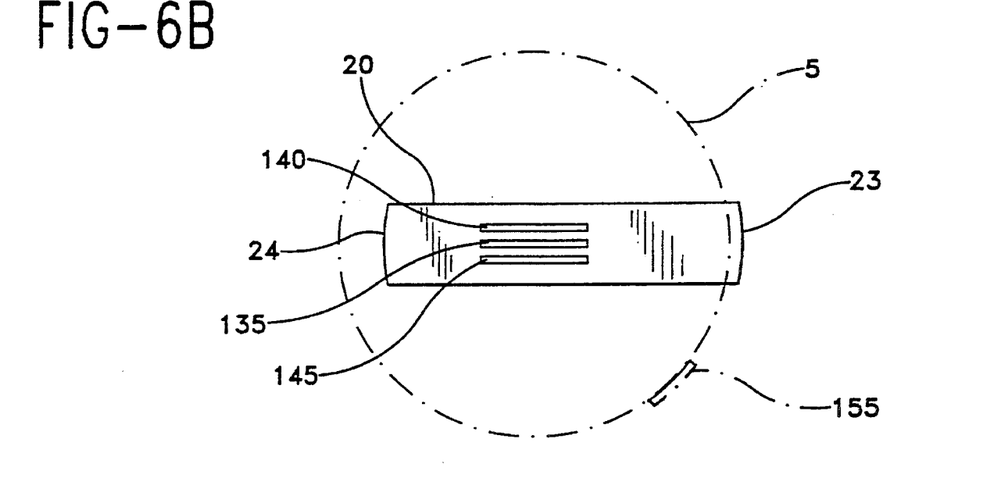
FIG. 6B is a top plan view of the wearable iontophoresis system of the present invention with the control housing in phantom showing a second arrangement of the control housing electrical contacts.
Figure 6C:
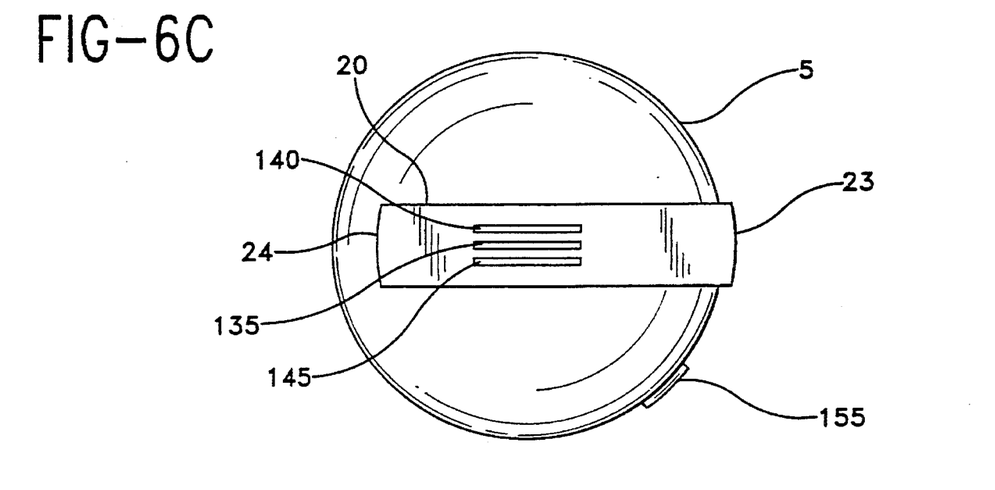
FIG. 6C is a bottom plan view of the wearable iontophoresis system of the present invention showing a third arrangement of the control housing electrical contacts.

As shown in FIGS. 6A, 6B and 6C, the first, second and third electrical contacts 135, 140, 145 of the control housing 5 may be located on a variety of control housing surfaces depending upon the location of the connector retaining means electrical contacts 120, 125, 130. The electrical contacts 135, 140, 145 may be located on the bottom surface 15 of control device 5 at a point which is adjacent to the connector means 20 as shown in FIG. 6A (connector means in phantom). Accordingly, with this configuration, the corresponding electrical contacts 120, 125, 130 of the connector retaining means 30 are preferably located on the top exterior surface of the arch-like portion 70 of the connector retaining means 30 as shown in FIG. 5A so as to electrically couple the control housing 5 and iontophoretic drug delivery patch 25. Alternatively, the control housing electrical contacts 135, 140, 145 may be located on the top surface 21 of the connector means 20 as shown in FIG. 6B (control housing in phantom) if the electrical contacts 120, 125, 130 of the patch 25 are located on a top, interior surface of the arch-like top portion of the connector retaining means 30 as shown in FIG. 5B. In another embodiment, the control housing electrical contacts 135, 140, 145 may be configured on the bottom surface 22 of the connector means 20 as shown in FIG. 6C, if the corresponding first, second and third electrical contacts 120, 125, 130 of the iontophoretic drug delivery patch 25 are located on the planar base portion 65 (as shown in FIG. 5C) of the connector retaining means 30.

Similar to the aforementioned symmetric arrangement of the second and third electrodes 95, 100, second and third electrical contacts 125, 130 of the patch 25 and second and third electrical contacts 140, 145 of the control housing 5 are respectively symmetric about a corresponding first electrical contact 120 or 135. As a result, the direction of mounting of the connector means 20 and control housing 5 to the connector retaining means 30 and patch 25 will not effect the operation and transfer of electrical signals from the control housing 5 to the iontophoretic drug delivery patch 25. This enables the iontophoretic system to be very "user friendly."

In a preferred embodiment and as shown in the figures, the connector means 20 takes the form of a male connector that can mate with the female-like connector retaining means 30 having cavity 75. In addition and as shown in FIG. 2A, the connector means thickness is tapered from the second end 24 to the first end 23. Preferably, the connector retaining means cavity 75 will have a cross-sectional shape substantially similar to a cross-section of the connector means 20. It is preferred that each of the first and second opposite open ends 80, 85 of the connector retaining means 30 are capable of receiving the connector means 20. The present invention is designed in this way so that the control housing 5 can be mounted to the patch in a manner most convenient to the user (i.e., either through the first open end 80 or the second open end 85). In addition, the size of the first and second opposite open ends 80, 85 and the size of the connector retaining means cavity 75 are preferably configured such that the first end of the connector means 20 is precluded from being inserted into cavity 75 past a point where contacts 135, 140, 145 of the connector means are electrically coupled to the contacts 120, 125, 130 of the connector retaining means 30. As a result, if the user inserts the connector means into the cavity to a point where the connector cannot be inserted further, the corresponding electrical contacts of the control housing and patch will couple so that electrical signals can pass to and from the housing and patch.

Referring again to FIG. 4 of the drawings, the control housing 5, which removably attaches to the iontophoretic drug delivery patch 25, also includes power supply means 150, on/off switch means 155, and current delivery circuit 160 as known in the art for controlling the amount of medicine delivered to the applied area of the patient.

The wearable iontophoretic drug delivery system 1 of the present invention also includes a target area region 152 located on the top surface 55 of the iontophoretic drug delivery patch 25. The target area serves to identify the orientation and size of the first electrode 90 from an elevated top view. This is practicle because the first electrode is not readily visible to the user during placement since it is located on the bottom surface 60 of the patch 25. The first electrode 90 corresponds to the region of the patch 25 which delivers the ionic medicine to the patient. With the aid of the target area 150, the user is able to appropriately position the patch 25 on the skin so that the medicine can be administered to the intended applied area. In another embodiment, the target area corresponds to the boundaries of the first connection means 30 so that a separate target area region need not be included. In still another embodiment, the target area is designated by a ,color which is substantially different than the color of the other portions of the top surface of the iontophoretic drug delivery patch.

The present invention serves to facilitate monitoring the operation of the drug delivery system by a user by including indicator lights 50. As a result of the orientation of the indicator light, 50, if a user has the wearable iontophoretic drug delivery system 1 attached to a portion of his/her body wherein the user is unable to view the indicator lights 50 from a direction substantially perpendicular to the top surface of the control housing 5 (for example if the device is attached to the patient's torso), the user will also have the opportunity to view the indicator lights 50 from an orientation which is substantially parallel to the top surface of the control housing and therefore easily monitor the operation of the device (see FIG. 2B). As a result of the design of the present invention, the user can view the indicator lights 50 and monitor the operation of the iontophoretic drug delivery device 1 without prematurely uncoupling the control housing 5 from the patch 25 or without removing the entire iontophoresis system from his/her body.

In a preferred embodiment, the control housing 5 also includes an on/off switch 155 coupled to the power supply means 150 for activating and deactivating the power supply. The on/off switch 155 is preferably located on the circumference of the control housing 5 at a position which is distal with respect to both the first and second ends 23, 24 of the connector means 20. As a result of this configuration, the user will have a reduced likelihood of unintentionally hitting the on/off switch when the control housing 5 is manipulated for the purpose of mounting to, or removal from, the iontophoretic drug delivery patch 25.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed:

1. A wearable iontophoretic drug delivery system for delivering medication to an applied area of a patient comprising:

a control housing containing at least power supply means for providing electric power and current delivery means for providing electric current, the control housing having top and bottom surfaces and connector means, the connector means having first and second ends defining a connector length, the connector means second end being attached and the connector means first end being unattached to the control housing, the connector means having top and bottom surfaces, at least one of the top and bottom surfaces being attached to the control housing, the connector means having a thickness defined by the connector means top and bottom surfaces; and an iontophoretic drug delivery patch for placement against the skin of a patient, the iontophoretic drug delivery patch being flexible and including top and bottom surfaces, the top surface of the patch having connector retaining means for retaining the control housing connector, the connector retaining means being defined by a substantially planar base portion and a non-planar top portion, the non-planar top portion being attached to the planar base portion, the non-planar top portion and planar base portion defining a connector retaining means cavity, the connector retaining means cavity having first and second open ends, the first and second open ends having substantially the same size aperture, the aperture of the first and second ends and the cross section of the connector retaining means cavity having a size suitable for at least partial placement of the connector means therein.

2. A wearable iontophoretic drug delivery system for delivering medication to an applied area of a patient as defined by claim 1 wherein one of the control housing and connector means includes first and second electrical contacts coupled to the current delivery means and power supply means, and wherein the iontophoretic drug delivery patch includes third and fourth electrical contacts, and wherein when the first end of the connector means of the control housing is at least partially inserted within one of the first and second open ends of the connector retaining means, the first and second electrical contacts of the control housing are respectively coupled to the third and fourth electrical contacts of the patch.

3. A wearable iontophoretic drug delivery system for delivering medication to an applied area of a patient as defined by claim 2 wherein the iontophoretic drug delivery patch includes first and second electrodes, the iontophoretic drug delivery patch including ionic medication holding means for containing ionic medication situated in relation to the first electrode such that ionic medication held by the ionic medication holding means is in electrical communication with the first electrode, the iontophoretic drug delivery patch including electrolyte holding means for containing electrolyte situated in relation to the second electrode such that an electrolyte held by the electrolyte holding means is in electrical communication with the second electrode, the third and fourth electrical contacts respectively being in electrical communication with the first and second electrodes.

4. A wearable iontophoretic drug delivery system for delivering medication to an applied area of a patient as defined by claim 3 further comprising a target area, the target area being located on the top surface of the iontophoretic drug delivery patch, the target area corresponding to and identifying the position and orientation of the first electrode on the bottom surface of the patch, the first electrode corresponding to the region of the iontophoretic drug delivery patch which delivers the ionic medication.

5. A wearable iontophoretic drug delivery system for delivering medication to an applied area of a patient as defined by claim 4 wherein the target area is defined by the connector retaining means.

6. A wearable iontophoretic drug delivery system as defined by claim 4 wherein the color of the target area is substantially distinct from the color of the top surface of the iontophoretic drug delivery patch.

7. A wearable iontophoretic drug delivery system for delivering medication to fan applied area of a patient as defined by claim 3 wherein when the third and fourth electrical contacts of the iontophoretic drug delivery patch are respectively electrically coupled to the first and second electrical contacts of the control housing, electrical signals can be provided from the control housing to the first and second electrodes of the iontophoretic drug delivery patch so as to induce ionic medication to leave the ionic medication holding means and infuse the skin of the patient.

8. A wearable iontophoretic drug delivery system for delivering medication to an applied area of a patient as defined by claim 2 wherein the non-planar top portion of the connector retaining means includes interior and exterior surfaces, and wherein the third and fourth electrical contacts are located on the interior surface of the non-planar top portion of the iontophoretic drug delivery patch, and wherein the first and second electrical contacts are located on the top surface of the connector means such that when the first end of the connector means is at least partially inserted within one of the first and second open ends, the first and second electrical contacts are electrically coupled to the third and fourth electrical contacts.

9. A wearable iontophoretic drug delivery system for delivering medication to an applied area of a patient as defined by claim 2 wherein the non-planar top portion of the connector retaining means includes interior and exterior surfaces, and wherein the third and fourth contacts are located on the exterior surface of the non-planar top portion of the iontophoretic drug delivery patch, and wherein the first and second electrical contacts are located on the bottom surface of the control housing such that when the first end of the connector means is at least partially inserted within one of the first and second open ends, the first and second electrical contacts are electrically coupled to the third and fourth electrical contacts.

10. A wearable iontophoretic drug delivery system for delivering medication to an applied area of a patient as defined by claim 2 wherein the third and fourth electrical contacts are located on the substantially planar base portion of the connector retaining means, the third and fourth electrical contacts being located within the connector retaining means cavity of the iontophoretic drug delivery patch, and wherein the first and second electrical contacts are located on the bottom surface of the connector means of the control housing such that when the connector means is at least partially inserted within one of the first and second open ends, the first and second electrical contacts are coupled to the third and fourth electrical contacts.

11. A wearable iontophoretic drug delivery system for delivering medication to an applied area of a patient as defined by claim 2 wherein the connector means has a first thickness at the first end and a second thickness at the second end, the second thickness being greater than the first thickness, the connector means thickness being tapered along the length of the connector means from the second end to the first end, the thickness of the connector means as compared to the size of the first and second open ends is such that when the first end of the connector means is inserted through one of the first and second open ends into the connector retaining means cavity, the size of the respective open end restricts the connector means from being inserted into the cavity past a point where the first and second electrical contacts are electrically coupled to the third and fourth electrical contacts.

12. A wearable iontophoretic drug delivery system for delivering medication to an applied area of a patient as defined by claim 3, the iontophoretic drug delivery patch further including a third electrode, the electrolyte holding means being situated in relation to the third electrode such that the electrolyte held by the electrolyte holding means is in electrical communication with the third electrode, the iontophoretic drug delivery patch having a sixth electrical contact in electrical communication with the third electrode, the control housing having a fifth electrical contact, wherein when the first end of the connector means is inserted within one of the first and second open ends of the connector retaining means cavity, the fourth and sixth electrical contacts of the iontophoretic drug delivery patch are respectively electrically coupled to one of the second and fifth electrical contacts of the control housing and connector means.

13. A wearable iontophoretic drug delivery system for delivering medication to an applied area of a patient as defined by claim 11 wherein the iontophoretic drug delivery patch further comprises a second electrolyte holding means for containing electrolyte situated in relation to the third electrode such that an electrolyte held by the second electrolyte holding means is in electrical communication with the third electrode.

14. A wearable iontophoretic drug delivery system for delivering medication to an applied area of a patient as defined by claim 11 wherein the first, second and third electrodes are located on the bottom surface of the iontophoretic drug delivery patch.

15. A wearable iontophoretic drug delivery system for delivering medication to an applied area of a patient as defined by claim 11 wherein the second and third electrodes of the iontophoretic drug delivery patch are symmetric about the first electrode.

16. A wearable iontophoretic drug delivery system for delivering medication to an applied area of a patient as defined by claim 1 wherein the control device top surface includes raised, recessed and sloping portions, the raised portion and recessed portion being substantially parallel and non-coplanar with each other, the sloping portion coupling the raised portion and the recessed portion of the control device top surface.

17. A wearable iontophoretic drug delivery system for delivering medication to an applied area of a patient as defined by claim 1 wherein the connector means has a first thickness at the first end and a second thickness at the second end, the second thickness being greater than the first thickness wherein the connector means thickness tapers along the length of the connector means from the second end to the first end.

18. A wearable iontophoretic drug delivery system for delivering medication to an applied area of a patient as defined by claim 1 wherein the non-planar top portion of the connector retaining means has an arch-like shape.

19. A wearable iontophoretic drug delivery system for delivering medication to an applied area of a patient as defined by claim 1, the control housing further comprising an on/off switch coupled to the power supply means for activating and deactivating the power supply means.

20. A wearable iontophoretic drug delivery system for delivering medication to an applied area of a patient as defined by claim 19, the control housing further comprising first indicator means coupled to the on/off switch for denoting when the wearable iontophoretic drug delivery device is operating.

21. A wearable iontophoretic drug delivery system for delivering medication to an applied area of a patient as defined by claim 19, the control housing further comprising second indicator means for denoting when the wearable iontophoretic drug delivery device has completed delivery of the ionic medication.

22. A wearable iontophoretic drug delivery system for delivering medication to an applied area of a patient as defined by claim 20, the control housing further comprising third indicator means for denoting when one of the third and fourth electrical contacts of the iontophoretic drug delivery patch is respectively improperly coupled to one of the first and second electrical contacts of the control housing and connector means.

23. A wearable iontophoretic drug delivery system for delivering medication to an applied area of a patient as defined by claim 19 wherein the first indicator means is located on the top surface of the control device, the first indicator means extending along the top surface of the control device from the raised portion across the sloping portion to the recessed portion so that the first indicator means is visible from an orientation which is substantially perpendicular to the top surface of the control device and from at least one orientation which is substantially parallel to one of the raised and recessed portions of the top surface of the control device.

24. A wearable iontophoretic drug delivery system for delivering medication to an applied area of a patient as defined by claim 19 wherein the on/off switch is circumferentially located on the control device at a position which is distal with respect to both the first and second ends of the connector means.

25. A wearable iontophoretic drug delivery system for delivering medication to an applied area of a patient as defined by claim 1 further comprising attachment means for securing the iontophoretic drug delivery patch to the applied area of the patient.

26. A wearable iontophoretic drug delivery system for delivering medication to an applied area of a patient as defined by claim 25 wherein the attachment means comprises adhesive material provided to the bottom surface of the iontophoretic drug delivery patch, the adhesive means permitting the iontophoretic drug delivery patch to be secured to the skin of the patient.

27. A wearable iontophoretic drug delivery system for delivering medication to an applied area of a patient for delivering medication to an applied area of a patient as defined by claim 1 wherein the iontophoretic drug delivery patch further includes a middle section and first and second end sections, each section of the patch having a width, the width of the middle section being substantially uniform, the first and second end sections each having a tapered width from a point proximate to the middle section to an end of the patch distal to the middle section.

* * * * *